(12) United States Patent
Hoffmann et al.

(10) Patent No.: US 6,765,119 B2
(45) Date of Patent: Jul. 20, 2004

(54) METHOD OF PRODUCING SATURATED $C_3$-$C_{20}$-ALCOHOLS

(75) Inventors: Herwig Hoffmann, Frankenthal (DE); Michael Röper, Wachenheim (DE); Heinrich-Josef Blankertz, Forst (DE); Max Strohmeyer, Limburgerhof (DE); Helmut Walz, Ludwigshafen (DE); Helmut Zinke-Allmang, Bad Dürkheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/276,219

(22) PCT Filed: May 17, 2001

(86) PCT No.: PCT/EP01/05676
§ 371 (c)(1),
(2), (4) Date: Nov. 14, 2002

(87) PCT Pub. No.: WO01/87809
PCT Pub. Date: Nov. 22, 2001

(65) Prior Publication Data
US 2003/0114720 A1 Jun. 19, 2003

(30) Foreign Application Priority Data
May 18, 2000 (DE) ......................................... 100 24 542

(51) Int. Cl.$^7$ .......................... C07C 29/14; C07C 29/16; C07C 27/04; C07C 27/00; C07C 27/02

(52) U.S. Cl. ....................... 568/881; 568/876; 568/878; 568/880; 568/882; 568/883; 568/884; 568/885

(58) Field of Search ................................. 568/876, 878, 568/880, 881, 882, 883, 884, 885

(56) References Cited

FOREIGN PATENT DOCUMENTS

| | | |
|---|---|---|
| DE | 16 43 856 | 11/1971 |
| DE | 26 28 987 | 1/1978 |
| EP | 0 004 122 | 9/1979 |
| GB | 2 097 390 | 11/1982 |
| WO | WO 96/26173 | 8/1996 |
| WO | WO 99/31035 | 6/1999 |

OTHER PUBLICATIONS

CRC Handbook of Chemistry and Physics 76$^{th}$ Ed. 1995–1996 pp. 8–43–44.

Organikum No. 16 (1986) pp. 138.

Peter Sykes "Reaktionsmechanismen der Organischen Chemie" No. 8 (1982) pp. 306–307.

*Primary Examiner*—Johann Richter
*Assistant Examiner*—Elvis O. Price
(74) *Attorney, Agent, or Firm*—Keil & Weinkauf

(57) ABSTRACT

The invention relates to a process for the preparation of saturated $C_3$–$C_{20}$-alcohols in which a liquid hydrogenation feed comprising at least one $C_3$–$C_{20}$-aldehyde is passed over a bed of a hydrogenation catalyst in the presence of a hydrogen-containing gas, which comprises adding to the hydrogenation feed an amount, homogeneously soluble therein, of a salt-like base. The addition of base suppresses side reactions, such as acetalization, aldolization, Tischtschenko reaction or ether formation.

5 Claims, No Drawings

METHOD OF PRODUCING SATURATED C$_3$-C$_{20}$-ALCOHOLS

This application is a 371 of PCT/EP01/05676, filed May 5, 2001.

The present invention relates to a process for the preparation of saturated C$_3$–C$_{20}$-alcohols in which a liquid hydrogenation feed comprising at least one C$_3$–C$_{20}$-aldehyde is passed over a bed of a hydrogenation catalyst in the presence of a hydrogen-containing gas.

The catalytic hydrogenation of aldehydes in order to obtain alcohols is a process which has been carried out on an industrial scale for decades and in which a multiplicity of catalysts, which generally consist of elements from subgroups VI to VIII and I of the Periodic Table, in particular of the elements chromium, manganese, iron, cobalt, nickel and/or copper, are employed. Such catalysts are described, for example, in DE-A 32 28 881, DE-A 26 28 987 and DE-A 24 45 303. The alcohols prepared by these processes find broad use, for example as solvents or as plasticizer alcohols.

In the hydrogenation, in particular at high hydrogenation temperatures, undesired side reactions, such as acetalization or aldolization, the Tischtschenko reaction or ether formation, occur in addition to the desired hydrogenation of the aldehyde to the alcohol. These side reactions result in a reduction in the product yield and require increased effort during purification of the hydrogenation product in order to obtain the relevant alcohol in the desired purity.

In order to avoid side reactions of this type, DE-A 26 28 897 recommends adding water to the hydrogenation feed. However, this measure has a number of disadvantages; for example, the energy necessary for purification of the resultant alcohols by distillation increases significantly.

Another possibility for reducing the formation of by-products comprises increasing the hydrogen pressure in the hydrogenation, which increases the rate of the hydrogenation reaction, while the reaction rate of the side reactions which are independent of the hydrogen pressure remains the same. Overall, the selectivity with respect to the desired hydrogenation product thus increases.

However, an increase in the hydrogen pressure is associated with high equipment complexity, since, for safety reasons, pressurized reactors with thicker walls must be used and further safety precautions have to be taken.

German patent 16 43 856 describes the hydrogenation of aldehydes by means of a copper- and/or nickel-containing catalyst whose surface has been adjusted to a pH of from 6 to 10 by treatment with alkali metal hydroxides. This publication is expressly directed to the use of the catalysts pretreated in this way in gas-phase hydrogenation. Their use in liquid-phase hydrogenation is only possible to a limited extent. The alkali metal hydroxide is usually washed out by the liquid hydrogenation feed or the liquid hydrogenation products and removed from the reaction system, and consequently the advantages of the surface treatment of the catalyst are only short term.

JP 172 838 A relates to the hydrogenation of C$_5$- and higher aldehydes on a nickel/chromium catalyst in the presence of a tertiary aliphatic amine.

JP 171 447 A relates to the hydrogenation of C$_4$-aldehydes to butanol on a nickel/chromium catalyst in the presence of a tertiary aliphatic amine. In both the last-mentioned processes, the added amine is separated off from the hydrogenation product by subsequent distillation and advantageously fed back into the hydrogenation. However, pure amine is not recovered in the distillation, but instead a mixture of the amine with so-called high boilers, i.e. the by-products which boil higher than the target alcohol and are formed in the hydrogenation of aldehydes, is obtained. The recycling of the amine/high boiler mixture requires that a ballast of high boilers is always circulated through the hydrogenation and distillation. Since, in order to avoid increases in concentration, a part of the high-boilers which corresponds to the formation rate of the high boilers must always be removed from the circuit, amine losses are unavoidable and represent an additional economic burden for the process.

WO 96/26173 describes a process for the purification of C$_3$–C$_{10}$-alcohols by distillation, where the distillation is carried out in the presence of an alkali metal hydroxide. This publication makes no mention of the addition of a salt-like base to a liquid hydrogenation feed.

It is an object of the present invention to indicate a process for the preparation of saturated alcohols from aldehydes by liquid-phase hydrogenation in which the formation of undesired by-products is suppressed, in particular at hydrogenation temperatures of 150° C. or above, and which is free from the disadvantages of the known hydrogenation processes.

We have found that this object is achieved by a process in which a liquid hydrogenation feed comprising at least one C$_3$–C$_{20}$-aldehyde is passed over a bed of a hydrogenation catalyst in the presence of a hydrogen-containing gas, which comprises adding to the hydrogenation feed an amount, homogeneously soluble therein, of a salt-like base $[M^+]_n[A^{n-}]$, in which $[M^+]$ is an alkali metal ion or the equivalent of an alkali earth metal ion; $[A^{n-}]$ is an anion of an acid having a pK$_s$ value of greater than 2, and n is the valency of the anion.

The effect of the addition of base to the hydrogenation feed is that the side reactions outlined at the outset are substantially suppressed even at hydrogenation temperatures of 150° C. or above, and very pure alcohols are obtained even at these hydrogenation temperatures.

The type of salt-like base used is generally not crucial so long as the salt-like base used is homogeneously soluble in the hydrogenation feed, at least in low concentration, and does not undergo any undesired side reactions with the aldehyde. Accordingly, a multiplicity of salt-like bases can successfully be employed in the process according to the invention.

The bases employed in accordance with the invention are salt-like, i.e. they are built up from cations and anions; they comprise at least one alkali metal or alkaline earth metal cation, such as lithium, sodium, potassium, magnesium or calcium ions, and a basic anion. The corresponding acid of the basic anion has a pK$_a$ value of greater than 2, preferably greater than 4, in particular greater than 8. The pK$_a$ value used for the characterization of the acid strength of the corresponding acid is the negative decimal logarithm of the dissociation constant of the acid in dilute aqueous solution. The pK$_a$ values of numerous acids have been tabulated and are given, for example, in CRC Handbook of Chemistry and Physics, 76$^{th}$ Edn., 1995, CRC Press; Organikum, various authors, 16$^{th}$ Edn., VEB Deutscher Verlag der Wissenschaften 1986, p. 138; Sykes P., Reaktionsmechanismen der Org. Chemie, 8$^{th}$ Edn. 1982, p. 307.

Suitable basic anions are hydroxide (14), carbonate (10.33), hydrogencarbonate (6.35), phosphate (12.35), amide (35), hydride (39); alkoxides, in particular C$_1$–C$_4$-alkoxides, such as methoxide (16), ethoxide, n- and isopropoxide and butoxide; phenoxide (10), carboxylates, such as acetate (4.76) or benzoate (4.21); carbanions, such as butyl (50), cyclopentadienyl or phenyl (40). The values in brackets indicate the $pK_S$ value of the respective corresponding acid. Besides the hydride ion itself, complex hydrides are also suitable; these can be regarded as adducts of the hydride ion and their basicity is essentially due to the, hydride ion, for example complex hydrides such as $[BH_4]^-$ or $[BHR_3]^-$ (where $R=C_1-C_4$-alkyl, for example s-butyl).

In general, hydroxide or carbonate is preferred.

Advantageous salt-like bases are, in particular, alkali metal hydroxides and/or carbonates, such as lithium carbonate, potassium carbonate, sodium carbonate, lithium hydroxide, sodium hydroxide and potassium hydroxide. In general, sodium hydroxide and/or potassium hydroxide are preferred. However, sodium alkoxides and/or potassium alkoxides, such as the methoxide or ethoxide, or the alkoxide of the alcohol which is the hydrogenation product of the aldehyde present in the hydrogenation feed can also be employed with particular advantage.

The salt-like bases are generally added to the hydrogenation feed in an amount which corresponds, on neutralization equivalent basis, to from 0.1 to 2000 ppm by weight, preferably from 0.1 to 1000 ppm by weight, in particular from 0.1 to 100 ppm by weight, particular preferably from 0.5 to 50 ppm by weight and in particular from 1 to 20 ppm by weight, based on the aldehyde present in the hydrogenation feed, of potassium hydroxide. In the case of monovalent basic anions, a molar amount of salt-like base which corresponds to the stated amount of potassium hydroxide is used, and in the case of divalent basic anions, half the molar amount is used. It is also possible to add mixtures of different bases.

Owing to the low salt-like base concentrations employed and the generally low price of these bases, recovery is not necessary or advantageous.

The liquid hydrogenation feed can consist of one or more undiluted aldehydes. However, the aldehydes are preferably employed as a solution in an inert diluent. Examples of suitable inert diluents are hydrocarbons, ethers, such as diethyl ether, or alcohols. The diluents are particularly preferably alcohols, in particular the alcohol which is the hydrogenation product of the aldehyde to be hydrogenated. In a preferred embodiment, a part amount of the hydrogenation product is recycled for this purpose and mixed with the aldehyde to be hydrogenated. If used, the inert diluent is preferably used in an amount of from 0.1 to 100 parts by weight, in particular from 1 to 50 parts by weight and particularly preferably from 5 to 20 parts by weight, based on one part by weight of aldehyde employed. If the hydrogenation is carried out adiabatically, i.e. with removal of the heat of reaction by the reaction product, the amount of inert diluent used is advantageously such that the temperature gradient over the bed of the granular catalyst does not exceed 40° C. If, by contrast, the hydrogenation reactor is operated isothermally, the proportion of inert diluent in the hydrogenation feed can be selected virtually as desired.

The hydrogenation feed generally contains traces of water, for example in the order of from 1 ppm to 1% by weight, which have been introduced by the starting materials in the preceding synthesis steps or formed by condensation reactions. These traces of water are unimportant for the process according to the invention. On use of salt-like bases other than hydroxides, hydroxide ions are formed therefrom by transprotonation and/or hydrolysis, which is in accordance with the invention.

The process according to the invention can be carried out either batchwise or continuously, for example with the aid of tubular reactors or reactor cascades. The catalyst bed generally rests on a suitable retention element in the reactor. The hydrogenation reactor can be operated either by the pool or trickle method. The process according to the invention is preferably carried out in a reactor cascade, in particular a cascade comprising two to five reactors.

The salt-like base can be added in solid or dissolved form; it is preferably added in the form of its solution in water or an alcohol, in particular the alcohol which is the hydrogenation product of the aldehyde present in the hydrogenation feed. For example, from 1 to 40 percent by weight solutions are suitable. The base and the hydrogenation feed can be introduced into the hydrogenation reactor separately from one another, with the mixture of base and hydrogenation feed forming in situ in the reactor. In particular in the case of the continuous procedure, however, a preformed mixture of based and hydrogenation feed is preferably passed into the reactor. If, as in a preferred embodiment, a part amount of the hydrogenation product is fed back as diluent before the hydrogenation reactor, the metering of the base is advantageously carried out into the return stream before the latter is mixed with the aldehyde to be hydrogenated. In this way, local concentration maxima of the base during contact with the aldehyde, which can result in undesired aldolization, are avoided. If a reactor cascade is used, the requisite amount of base can be passed into the first reactor of the cascade together with the hydrogenation feed; however, it is also possible to meter the base separately into each individual reactor of the cascade. The total amount of base is preferably fed into the first reactor of the cascade together with the hydrogenation feed.

The hydrogenation catalyst used is one of the catalysts usually used for the hydrogenation of aldehydes to alcohols. The type of catalyst used is not a subject-matter of the present invention; the advantageous effects achieved by the process according to the invention are generally independent of the type of hydrogenation catalyst used. Accordingly, a multiplicity of hydrogenation catalysts can be used in the process according to the invention, for example metal-containing supported catalysts with metals from sub-group(s) I, VII and/or VIII of the Periodic Table as catalytically active components, in particular supported catalysts with rhenium, platinum, palladium, rhodium and/or ruthenium as catalytically active components and support materials such as aluminum oxide, titanium dioxide, silicon dioxide, zirconium dioxide or barium sulfate; or precipitation catalysts comprising at least one element from sub-group(s) I, VI, VII and/or VIII of the Periodic Table, for example catalysts as described in DE-A 32 28 881, DE-A 26 28 987 and DE-A 24 45 303. The catalysts are preferably in granular form and generally have a particle size of from 3 to 10 mm. The catalysts may be arranged in one or more beds in the reactor. Different catalysts can be used in the various beds of a reactor or in the various reactors of a reactor cascade.

The hydrogen-containing gas preferably comprises more than 80 mol % of hydrogen; in particular, it essentially consists of hydrogen. The hydrogen-containing gas can be passed over the hydrogenation catalyst bed in cocurrent or countercurrent to the hydrogenation feed. It is preferably passed in cocurrent. The amount of hydrogen-containing gas fed in is advantageously such that from 1.0 to 1.15 times the stoichiometrically necessary amount of hydrogen is available.

The hydrogenation of the alcohols can be carried out under conditions which are conventional per se. In general, elevated temperatures, for example from 100 to 300° C., preferably from 120 to 250° C. and in particular from 130 to 200° C., and pressures of from 1 to 700 bar, preferably from 5 to 300 bar and particularly preferably from 30 to 50 bar, are set. The catalysts are generally loaded with from 0.01 to 2, preferably with from 0.1 to 1 and in particular with from 0.2 to 0.5 l of aldehyde/l of catalyst per hour. The addition of water to the hydrogenation feed is possible in the process according to the invention, but is not necessary.

The alcohols are generally worked up by distillation by methods known per se.

The aldehydes to be hydrogenated are preferably aliphatic $C_3$- to $C_{20}$-, in particular $C_3$- to $C_{15}$-aldehydes, which may be straight-chain or branched and may additionally contain double bonds in the molecule. The aldehydes which can be employed are not subject to any restrictions in principle. Suitable aldehydes which are of particular economic importance are, for example, propanal, n-butanal, isobutyraldehyde, hexanal, ethylhexanal, ethylhexenal, nonenal, nonanal, decanal, decenal and the hydroformylation products of trimeric and tetrameric propylene and dimeric and trimeric butene.

The process according to the invention has a number of advantages:

The acetal and ether formation side reactions which occur during hydrogenation of aldehydes in the liquid phase are greatly suppressed. The addition of water to the hydrogenation feed which was customary hitherto can be reduced or omitted completely. This enables the energy consumption in the subsequent distillation of the hydrogenation product to be significantly reduced, since the water is generally distilled off at the top of the column. The hydrogenation temperature can be increased without the fear of an increase in side reactions. This enables the space-time yield to be increased; for example, an increase in the hydrogenation temperature from 140 to 150° C. in the hydrogenation of butanal allows the catalyst loading with butanal to be increased by 25% for the same butanol yield. An increase in ether formation on increasing the hydrogenation temperature, which is to be expected without addition of base, is not observed. The increase in the hydrogenation temperature liberates the heat of hydrogenation at a higher temperature level and can be utilized for generating steam at 4 bar, for example in the integrated heat system of the hydrogenation plant. This results in a considerable saving of energy.

The invention is illustrated in greater detail by the examples below.

EXAMPLES

The aldehydes were hydrogenated in a reactor cascade consisting of an adiabatically operated first reactor having a capacity of 1450 l and a second reactor operated isothermally at 130° C. having a capacity of 225 l.

The hydrogenation feed comprising n-butanal (obtained by hydroformylation of propene) and crude butanol was fed to the two reactors in such a way that the liquid hourly space velocity was not less than 20 m² per hour. The crude butanol with which the butanal was mixed in the hydrogenation feed had previously been taken off from the bottom of the first hydrogenation reactor by means of a circulation pump. The second reactor served as post-reactor in order fully to hydrogenate the butanol reacted only incompletely in the first reactor. The composition of the hydrogenation product was determined by gas chromatography before its distillation.

Example 1

Not According to the Invention 2900 kg of a modified Adkins catalyst (Lit.: J. Am. Chem. Soc. 51, 2430 (1929); J. Am. Chem. Soc. 54, 4678 (1932)), which, in the unreduced state, comprised 35% by weight of copper, calculated as Cu, 31% by weight of chromium, calculated as Cr, 2.0% by weight of barium, calculated as Ba, and 2.5% by weight of manganese, calculated as Mn, were subjected in the apparatus described above to a hydrogenation feed as indicated above which was composed of 325 parts by weight of n-butanal and 5000 parts by weight of circulated crude butanol. Before use, the Adkins catalyst had been reduced at 300° C. in a stream of hydrogen until water was no longer formed. The hydrogen pressure in the reactor was 40 bar, the temperature on entry into the catalyst bed was 103° C., and the temperature at the outlet of the first reactor was 132° C. The reactor was operated for 180 days in this manner. The crude butanol obtained had the following composition (anhydrous):

| | |
|---|---|
| n-butanol | 98.85% by weight |
| di-n-butyl ether | 0.11% by weight |
| butyl butyrate | 0.12% by weight |
| butyraldehyde di-n-butyl acetal | 0.89% by weight |

The carbonyl number in accordance with DIN 53 173 as a measure of the residual aldehyde content was determined as being 0.1 g/g of crude butanol. The carbonyl number is the amount of potassium hydroxide in mg which is equivalent to the amount of hydrogen chloride liberated from hydroxylammonium chloride on oximation of 1 g of substance.

Example 2

According to the Invention

As described in Example 1, a hydrogenation feed comprising 430 parts by weight of n-butanal and 5000 parts by weight of crude butanol was hydrogenated, with 3 ppm by weight of potassium hydroxide, based on the n-butanal supplied, being added to the hydrogenation feed. The temperature at the catalyst bed inlet was 102° C., and the temperature at the outlet was 137° C. The hydrogen pressure was 40 bar. The reaction product had the following composition (anhydrous):

| | |
|---|---|
| butanal | 0% by weight |
| n-butanol | 99.68% by weight |
| di-n-butyl ether | 0.01% by weight |
| butyl butyrate | 0.24% by weight |
| butyraldehyde di-n-butyl acetal | 0.07% by weight |

The carbonyl number, as a measure of the residual aldehyde content of the crude butanol, was 0.1 mg/g of crude butanol. The carbonyl number did not worsen even after an operating time of 60 days.

Example 3

According to the Invention

In the apparatus described above, a catalyst in accordance with DE-A 26 28 987, which, in the unreduced state, comprised 24% by weight of nickel, calculated as NiO, 8% by weight of copper, calculated as CuO, 2.0% by weight of manganese, calculated as MnO, from 66% by weight of $SiO_2$ as support material, was introduced into the reactor in reduced form. For the reduction, the catalyst had been treated at 200° C. in a stream of hydrogen until water no longer formed.

500 parts by weight of n-butanal, 15 parts by weight of water and 5000 parts by weight of circulated crude butanol were introduced at the top of the reactor, and such an amount of a solution of potassium hydroxide in n-butanol was metered into this mixture that the feed comprised 7 ppm by weight of potassium hydroxide, based on the supplied butanal. The pressure in the reactor was 38 bar, the temperature at the catalyst bed inlet was 126° C., and the temperature at the outlet from the first reactor has risen to 150° C.

The hydrogenation product had the following composition (anhydrous) after an operating time of 142 days:

| | |
|---|---|
| butanal | 0.01% by weight |
| n-butanol | 99.41% by weight |
| di-n-butyl ether | 0.04% by weight |
| butyl butyrate | 0.02% by weight |
| butyraldehyde di-n-butyl acetal | 0.53% by weight |

Example 4

Not According to the Invention 960 kg of a catalyst comprising 19.6% by weight of copper and 0.2% by weight of sodium on a support of silica gel beads having a diameter of 3–6 mm were installed in the apparatus described above. The catalyst was pre-reduced.

A hydrogenation feed comprising 425 parts by weight of n-butanal and 5000 parts by weight of circulated crude butanol was introduced at the top of the 1$^{st}$ reactor. The hydrogen pressure in the reactor was 36 bar, the temperature at the catalyst bed inlet was 81° C., and the temperature at the outlet from the first reactor was 115° C. The crude butanol obtained had the following composition (anhydrous):

| | |
|---|---|
| n-butanol | 99.44% by weight |
| di-n-butyl ether | 0.01% by weight |
| butyl butyrate | 0.01% by weight |
| butyraldehyde di-n-butyl acetal | 0.44% by weight |

The carbonyl number in accordance with DIN 53 173 as a measure of the residual aldehyde content was determined as being 0.15 mg/g of crude butanol.

Example 5

According to the Invention

As described in Example 4, a hydrogenation feed comprising 425 parts by weight of n-butanal and 5000 parts by weight of crude butanol was hydrogenated, with 32 ppm by weight of potassium hydroxide, based on the supplied n-butanal, being added to the hydrogenation feed. The temperature at the catalyst bed inlet was 81° C., and the temperature at the outlet was 111° C. The crude butanol obtained had the following composition (anhydrous):

| | |
|---|---|
| n-butanol | 99.81% by weight |
| di-n-butyl ether | 0% by weight |
| butyl butyrate | 0.04% by weight |
| butyraldehyde di-n-butyl acetal | 0.02% by weight |

The carbonyl number, as a measure of the residual aldehyde content, was <0.01 mg/g of crude butanol.

Example 6a

Not According to the Invention

As described in Example 4, 985 kg of a pre-reduced catalyst comprising 24.1% by weight of copper and 0.27% by weight of sodium on a support of silica gel beads having a diameter of 3–6 mm were installed.

The catalyst was subjected, as indicated above, to a hydrogenation feed comprising 650 parts by weight of n-butanal and 5000 parts by weight of circulated crude butanol.

The hydrogen pressure in the reactor was 36 bar, the maximum temperature in the first catalyst bed was 126° C., and the maximum temperature in the second reactor was 120° C. The reactor was operated in this way for 120 days. The crude butanol obtained had the following composition (anhydrous):

| | |
|---|---|
| n-butanol | 99.12% by weight |
| di-n-butyl ether | 0.01% by weight |
| butyl butyrate | 0.02% by weight |
| butyraldehyde di-n-butyl acetal | 0.78% by weight |

The carbonyl in accordance with DIN 53 173, as a measure of the residual aldehyde content, was determined as being 0.1 g/g of crude butanol.

Example 6b

According to the Invention

The hydrogenation apparatus was operated further under identical conditions as in Experiment 6a. 10 ppm by weight of potassium hydroxide, based on the supplied butanal, were added to the hydrogenation feed. Just 48 hours later, the product had the following composition:

| | |
|---|---|
| n-butanol | 99.82% by weight |
| di-n-butyl ether | 0% by weight |
| butyl butyrate | 0.05% by weight |
| butyraldehyde di-n-butyl acetal | 0.04% by weight |

The carbonyl number, as a measure of the residual aldehyde content, was 0.02 mg/g of crude butanol.

This example shows that the advantageous effects of the process according to the invention are also achieved in the case of catalysts which are already in extended use and the effects arise rapidly.

Example 7

A hydrogenation catalyst in accordance with DE-A 26 28 987 having the following composition was used:
  24% by weight of nickel, calculated as NiO
  8% by weight of copper, calculated as CuO
  2.2% by weight of manganese, calculated as $Mn_3O_4$
  0.6% by weight of sodium, calculated as $Na_2O$
  remainder $SiO_2$ The hydrogenation was carried out in the apparatus described above under the conditions indicated there. The two reactors were filled with a total of 1600 l of the catalyst pre-reduced at 300° C. in a stream of hydrogen.

The hydrogenation feed, which comprised from 360 to 475 kg of butanal mixture and 4200 kg of crude butanol, was fed to the two reactors in such a way that the liquid loading per m² of reactor cross section area was from 30 to 40 m³. The crude butanol had previously been taken from the hydrogenation product of the first reactor for the purposes of recycling. The temperature above the bed in the first, adiabatically operated reactor was about 30° C.

The composition of the hydrogenation products were determined by gas chromatography before distillation.

Four experiments were carried out. In Experiments A and B, no base was added (not according to the invention). In Experiments C and D according to the invention, in each case 10 ppm by weight of potassium hydroxide, based on the aldehyde feed, were metered in. The results are shown in the table below.

|  | A: | B: |
|---|---|---|
| Starting materials: | 370 kg of butanal mixture | 430 kg of butanal mixture |
|  | 4200 kg of crude butanol | 4200 kg of crude butanol |
| Temperature at the inlet to the 1st reactor: | 138° C. | 144° C. |
| Pressure: | 35 bar | 35 bar |

Composition of the hydrogenation product:

|  | A: | B: |
|---|---|---|
| Butanals: | 0.006% by weight | 0.007% by weight |
| Butanols: | 99.2% by weight | 99.44% by weight |
| Di-n-butyl ether: | 0.19% by weight | 0.32% by weight |
| Butyl butyrate: | 0.03% by weight | 0.03% by weight |
| Butyraldehyde di-butyl acetal: | 0.53% by weight | 0.57% by weight |

|  | C: | D: |
|---|---|---|
| Starting materials: | 430 kg of butanal mixture | 485 kg of butanal mixture |
|  | 4200 kg of crude butanol | 4200 kg of crude butanol |
| Base: | 10 ppm by weight of KOH | 10 ppm by weight of KOH |
| Temperature at the inlet to the 1st reactor: | 150° C. | 150° C. |
| Pressure: | 35 bar | 35 bar |

Composition of the hydrogenation product:

|  | C: | D: |
|---|---|---|
| Butanals: | 0.01% by weight | 0.02% by weight |
| Butanols: | 99.5% by weight | 99.44% by weight |
| Di-n-butyl ether: | 0.01% by weight | 0.02% by weight |
| Butyl butyrate: | 0.02% by weight | 0.02% by weight |
| Butyraldehyde di-butyl acetal: | 0.46% by weight | 0.50% by weight |

It follows from these results that the hydrogenation temperature and accordingly the space-time yield can be increased with the aid of the addition of base according to the invention without the increase in the hydrogenation temperature resulting in an increase in ether formation.

We claim:

1. A process for the preparation of saturated alcohols in which a liquid hydrogenation feed comprising at least one aldehyde selected from propanal, n-butanal, isobutyraldehyde, hexanal, ethylhexanal, ethylhexenal, nonenal, nonanal, decanal, decenal and the hydroformylation products of trimeric propylene, tetrameric propylene, dimeric butene or trimeric butene, is passed over a bed of a hydrogenation catalyst in the presence of a hydrogen-containing gas, which comprises adding to the hydrogenation feed an amount, homogeneously soluble therein, of a salt-like base $[M^+]_n [A^{n-}]$, in which $[M^+]$ is an alkali metal ion or the equivalent of an alkali earth metal ion; $[A^{n-}]$ is an anion of an acid having a $pK_s$ value of greater than 2, and n is the valency of the anion.

2. A process as claimed in claim 1, wherein the salt-like base used is an alkali metal hydroxide and/or an alkali metal carbonate.

3. A process as claimed in claim 1, wherein an amount of salt-like base which corresponds, on neutralization equivalent basis, to from 0.1 to 2000 ppm by weight, based on the aldehyde present in the hydrogenation feed, of potassium hydroxide is added to the hydrogenation feed.

4. A process as claimed in claim 1, wherein the hydrogenation feed comprises an inert diluent.

5. A process as claimed in claim 4, wherein the inert diluent used is the alcohol which is the hydrogenation product of the aldehyde present in the hydrogenation feed.

* * * * *